United States Patent
Choi et al.

(10) Patent No.: US 9,296,802 B2
(45) Date of Patent: Mar. 29, 2016

(54) TARGET-SPECIFIC NON-ANTIBODY PROTEIN AND METHOD FOR PREPARING THE SAME

(75) Inventors: Yoon Sup Choi, Busan (KR); Jun Ho Chung, Seoul (KR); Ji Ho Yoo, Seoul (KR); Hyun Soo Cho, Gyeonggi (KR); Su Min Yoon, Seoul (KR); Kyung Lock Kim, Busan (KR); Sung Ho Ryu, Gyeongbuk (KR); Sang Uk Kim, Gyeongbuk (KR)

(73) Assignee: POSTECH ACADEMY-INDUSTRY FOUNDATION, Gyeongbuk (KR)

( * ) Notice: Subject to any disclaimer, the term of this patent is extended or adjusted under 35 U.S.C. 154(b) by 1167 days.

(21) Appl. No.: 13/264,365

(22) PCT Filed: Apr. 14, 2010

(86) PCT No.: PCT/KR2010/002318
§ 371 (c)(1),
(2), (4) Date: Dec. 5, 2011

(87) PCT Pub. No.: WO2010/120121
PCT Pub. Date: Oct. 21, 2010

(65) Prior Publication Data
US 2012/0071419 A1 Mar. 22, 2012

Related U.S. Application Data

(60) Provisional application No. 61/169,636, filed on Apr. 15, 2009.

(51) Int. Cl.
C40B 30/02 (2006.01)
C07K 14/485 (2006.01)
C07K 1/00 (2006.01)
C12N 15/10 (2006.01)
(Continued)

(52) U.S. Cl.
CPC ............. *C07K 14/485* (2013.01); *C07K 1/00* (2013.01); *C12N 15/1089* (2013.01); *C40B 30/02* (2013.01); *G06F 19/18* (2013.01); *A61K 38/00* (2013.01); *G06F 19/16* (2013.01); *G06F 19/22* (2013.01)

(58) Field of Classification Search
None
See application file for complete search history.

(56) References Cited

PUBLICATIONS

Joachimak et al. (2006) Journal of Molecular Biology vol. 361 pp. 195 to 208.*

(Continued)

*Primary Examiner* — Christian Boesen
(74) *Attorney, Agent, or Firm* — Foley & Lardner LLP; Antoinette F. Konski

(57) ABSTRACT

The present invention relates to a method for preparing a target-specific non-antibody protein, and more particularly, to a method for preparing a target-specific non-antibody protein comprising the steps of: selecting non-antibody proteins having a structural complementarity with the target site of a target protein in a non-antibody protein library; calculating a binding energy of the selected non-antibody protein and the target protein; selecting a non-antibody protein having a favorable binding energy among the selected non-antibody proteins; selecting amino acid residues having a high binding energy among the interfacial amino acid residues of the selected non-antibody protein and the target protein; and substituting the selected amino acid residues with the amino acid residues having a low binding energy. In addition, the present invention relates to a target-specific non-antibody specifically binding with EGFR (Epidermal Growth Factor Receptor) domain 2, which is prepared by the method, and a cancer therapeutic composition comprising the same.

7 Claims, 9 Drawing Sheets

(51) Int. Cl.
  *G06F 19/18* (2011.01)
  *A61K 38/00* (2006.01)
  *G06F 19/16* (2011.01)
  *G06F 19/22* (2011.01)

(56) References Cited

PUBLICATIONS

Gilbreth et al. (Aug. 29, 2008) Journal of Molecular Biology vol. 381 pp. 407 to 418.*

Hey, T. et al. Oct. 2005) "Artificial, non-antibody binding proteins for pharmaceutical and industrial applications," Trends in Biotechnology, 23(10): 514-522.

Ogiso, H. et al. Sep. 20, 2002) "Crystal Structure of the Complex of Human Epidermal Growth Factor and Receptor Extracellular Domains," Cell, 110: 775-787.

Skerra, A. (2007) "Alternative non-antibody scaffolds for molecular recognition," Current Opinion in Biotechnology, 18: 295-304.

* cited by examiner

```
        10         20         30         40         50         60
MEEKKVCQGT SNKLTQLGTF EDHFLSLQRM FNNCEVVLGN LEITYVQRNY DLSFLKTIQE
        70         80         90        100        110        120
VAGYVLIAIN TVERIPLERL QIIRGNMYYE NSYALAVLSN YDANKTGLKE LPMRNLQEIL
       130        140        150        160        170        180
HGAVRFSNNP ALCNVESIQN RDIVSSDFLS NMSMDFQNHL GSCQKCDPSC PNGSCWGAGE
       190        200        210        220        230        240
ENCQKLTKII CAQQCSGRCR GKSPSDCCHN QCAAGCTGPR ESDCLVCRKF RDEATCKDTC
       250        260        270        280        290        300
PPLMLYNPTT YQMDVNPEGK YSFGATCVKK CPRNYVVTDH GSCVRACGAD SYEMEEDGVR
       310        320        330        340        350        360
KCKKCEGPCR KVCNGIGIGE FKDSLSINAT NIKHFKNCTS ISGDLHILPV AFRGDSFTHT
       370        380        390        400        410        420
PPLDPQELDI LKTVKEITGF LLIQAWPENR TDLHAFENLE IIRGRTKQHG QFSLAVVSLN
``` underlined: domain II (166-309)

SEQ ID NO: 1

FIG. 2

MSSILPFTPP IVKRLLGWKK GEQNGQEEKW CEKAVKSLVK KLKKTGQLDE LEKAITTQNV
NTKCITIPRS LDGRLQVSHR KGLPHVIYCR LWRWPDLHSH HELRAMELCE FAFNMKDEV
CVNPYHYQRV ETPVLPPVLV PRHT

SEQ ID NO: 2

ATGTCGTCCA TCCTGCCTTT CACTCCCCCG ATCGTGAAGC GCCTGCTGGG CTGGAAGAAG
GGCGAGCAGA ACGGGCAGGA GGAGAAATGG TGCGAGAAGG CGGTCAAGAG CCTGGTCAAG
AAACTCAAGA AGACCGGGCA GCTGGACGAG CTGGAGAAGG CCATCACCAC CCAGAACGTC
AACACCAAGT GCATCACCAT CCCCAGGTCC CTGGATGGCC GGTTGCAGGT GTCCCATCGG
AAGGGCTCC CTCATGTCAT CTACTGCCGC CTGTGGCGAT GGCCAGACCT GCACAGCCAC
CACGAGCTAC GGGCCATGGA GCTGTGTGAG TTCGCCTTCA ATATGAAGAA GGACGAGGTC
TGCGTGAATC CCTACCACTA CCAGAGAGTA GACACACCAG TTCTACCTCC TGTGTTGGTC
CCACGCCACA CA

SEQ ID NO: 6

FIG. 6

MSSILPFTPP TVKRLLGWKK GEQNGQEEKW CEKAVKSLVK KLKSTGQLDE LEKAITTQNV
NTKCITIPRS LDGRLQVSHR KGLPHVIYCR LWRWPDLHSH HELRAMGLCS FAFNMKKLEV
CVNPYHQRV ETPVLPPVLV PRHT

SEQ ID NO: 3

ATGTCGTCCA TCCTGCCTTT CACTCCCCCG ATCGTGAAGC CTGGAAGAAG
CCCGGAGCAG ACGGCCAGGA GGAGAAATGC TGCCAGAAGC CGGTGCAAGG
AAACTCAAGA GCTGACGGGC AGCTGGACGA GCTGGAGAAG GCCATCACCA CCCAGAACGTC
AACACCAAGT GCATCACCAT CCCCAGGTCC CTGGATGCC GGTTGCAGTG GTCCCATCGG
AAGGGCTCC CTCATGTCAT CTACTGCCGC CTGTGGCGA GGCCAGACCT GCACAGCCAC
CACGAGCTAC GGGCCATGGG TCCGCCTTCC TTCGCCTTCA ATATGAAGAA GTTGGAGGTC
TGCGTGAATC CCTACCACTA GAGACACCAG TTCTACCTCC TGTGTGGGTG
CCAGCCACA CA

SEQ ID NO: 7

FIG. 7

MSSILPFTPP IVKRLLGWKK GEONGQEEKW CEKAVKSLVK KLKLTGQLDE LEKAITTQNV
NTKCITIPRS LDGRLQVSHR KGLPHVIYCR LWRWPDLHSH HELRAMALCA FAFMKKCEV
CVNPYHYQRV ETPVLPPVLV PRHT

SEQ ID NO: 4

ATGTCGTCCA TCCTGCCTTT CACTCCCCCG ATCGTGAAGC GCCTGCTGGG CTGGAAGAAG
GGCGAGAGGA ACGGGCAGGA GGAGAAATGG TGCGAGAAGG CCGTGAAGAG CCTGGTCAAG
AAACTCAAGC TTACGGGGCA GCTGGACGAG CTGGAGAAGG CCATCACCAC GCAGAACGTC
AACACAAGT GCATCACCAT CCCCAGGTCC CTGGATGGCC GGTTGCAGGT GTCCCATCGG
AAGGGGCTCC CTCATGTCAT CTACTGCCGC CTGTGGCGAT GGCCAGACCT GCACAGCCAC
CACGAGCTAC GGGCCATGGC TTCGCCTTCA TGATGAAGAA TGTGAGGTC
TGCGTGAATC CCTACCACTA CCAGAGAGTA GAGACACCAG TTCTACCTCC TGTGTTGGTG
CCACGCCACA CA

SEQ ID NO: 8

FIG. 8

MSSILPFTPP IVKRLLGWKK GEQNGQEEKW CEKAVKSLVK KLKATGQLDE LEKAITTQNV
NTKCITIPRS LDGRLQVSHR KGLPHVIYCR LWRWPDLHSH HELRAMQLCI FAFLMKKPEV
CVNPYHYQRV ETPVLPPVLV PRHT

SEQ ID NO: 5

ATGTCGTCCA TCCTGCCTTT CACTCCCCCG ATCGTGAAGC GCCTGCTGGG CTGGAAGAAG
GGCGAGCAGA ACGGGCAGGA GGAGAAATGG TGCGAGAAGG CGGTCAAGAG CCTGGTCAAG
AAACTCAAGG CGACGGGGCA GCTGGACGAG CTGGAGAAGG CCATCACCAC GCAGAACGTC
AACACCAAGT GCATCACCAT CCCCAGGTCC CTGGATGGCC GGTTGCAGGT GTCCCATCGG
AAGGGGCTCC CTCATGTCAT CTACTGCCGC CTGTGGCGAT GGCCAGACCT GCACAGCCAC
CACGAGCTAC GGGCCATGCA GCTGTGTATT TTCGCCTTCC TGATGAAGAA GCCGGAGGTC
TGCGTGAATC CCTACCACTA CCAGAGAGTA GAGACACCAG TTCTACCTCC TGTGTTGGTG
CCACGCCACA CA

SEQ ID NO: 9

FIG. 9

TARGET-SPECIFIC NON-ANTIBODY PROTEIN AND METHOD FOR PREPARING THE SAME

CROSS-REFERENCE TO RELATED APPLICATIONS

This application is a national stage application under 35 U.S.C. §371 of International Application No. PCT/KR2010/002318, filed Apr. 14, 2010, which claims the benefit under 35 U.S.C. §119(e) of U.S. Provisional Application Ser. No. 61/169,636, filed Apr. 15, 2009, the contents of which are hereby incorporated by reference into the present disclosure.

SEQUENCE LISTING

The instant application contains a Sequence Listing which has been submitted in ASCII format via EFS-Web and is hereby incorporated by reference in its entirety. Said ASCII copy is named 101351-0201_SL.txt and is 11,487 bytes in size.

BACKGROUND OF THE INVENTION

1. Field of the Invention

The present invention relates to a method for preparing a target-specific non-antibody protein, and more particularly, to a method for preparing a target-specific non-antibody protein comprising the steps of: selecting non-antibody proteins having a structural complementarity with the target site of a target protein in a non-antibody protein library; calculating a binding energy of the selected non-antibody protein and the target protein; selecting a non-antibody protein having a favorable binding energy among the selected non-antibody proteins; selecting amino acid residues having high binding energy among the interfacial amino acid residues of the selected non-antibody protein and the target protein; and substituting the selected amino acid residues with the amino acid residues having low binding energy. In addition, the present invention relates to a target-specific non-antibody specifically binding with EGFR (Epidermal Growth Factor Receptor) domain 2, which is prepared by the method, and a cancer therapeutic composition comprising the same.

2. Description of the Related Art

Conventionally, antibodies have been used as new therapeutic protein drugs. Antibodies are proteins produced by white blood cells called B lymphocytes in the immune system as a result of stimulation by an antigen. When antibodies encounter antigens, they recognize and bind to the antigens via receptors on the cells. Characteristically, antibodies specifically recognize and strongly bind to a particular protein. Due to this characteristic of binding to disease-causing proteins such as cancer, antibodies have been used for the purpose of preventing malicious protein interactions.

However, therapeutic antibodies have a large molecular size, their mass production is difficult, and their production process requires long processing times and high costs. Alternatively, recent studies have been actively conducted on non-antibody protein scaffolds for patient-tailored and targeted therapies. The non-antibody protein is a novel class of drug for patient-tailored and targeted therapies, and has begun to attract attention recently as an alternative to overcome the limitations of current therapeutic antibodies that has gained interest in present drug markets. Like therapeutic antibodies, the non-antibody proteins are aimed at treating various diseases such as cancer and autoimmune diseases or at preventing progression of diseases by selectively recognizing particular target molecules and strongly binding thereto so as to inhibit activity of the target molecules.

However, the existing non-antibody proteins are prepared relying on single scaffolds regardless of structures of the target molecules, like the conventional antibodies. Based on the tertiary structure, proteins bind to each other by interlocking together like Lego pieces. Thus, it is ideal to use tailored protein scaffolds specific to the particular targets. However, there are no technologies to find non-antibody proteins having a structural complementarity, capable of specifically binding to the target. Problematically, it is difficult to find target-specific non-antibody proteins used for the treatment of diseases. Experimentally, it is impossible to identify which proteins specifically bind to the particular target, because of diversity in the structure and type of proteins.

With respect to the existing antibodies and non-antibody proteins based on single scaffolds, their target site-binding region is accidentally determined, and thus the binding region cannot be designed in advance. In addition, the target sites bound by the known non-antibody proteins and antibodies are structurally restricted. It is fundamentally impossible to approach the concave target site. Inconveniently, a complex process for candidate screening, such as epitope mapping, should be performed for a long period of time, in order to find proteins capable of binding to a desired region of the target molecule among the target molecule-binding proteins.

In order to overcome the limitations of existing antibodies and non-antibody proteins, there is an urgent need to develop a technology for selecting scaffolds optimized for a target so as to design non-antibody proteins that bind to the desired target site of the target molecule. The technology for designing and preparing non-antibody proteins having a strong binding ability and specificity to the desired site of the target protein is a platform technology applicable to a wide range of target proteins, and this technology has not been realized in new antibody drugs or aptamers. Therefore, it is also urgently needed for the development of progressive patient-tailored and targeted therapies.

The present inventors have made an effort to develop a method for preparing target-specific non-antibody proteins. As a result, they found that virtual screening of a desired target site of a given target protein is performed based on a structural library of proteins with the predetermined tertiary structure so as to select an optimal protein scaffold having the highest structural complementarity, and randomization of amino acids that interfere with the binding to the target molecule is performed by phage display and bio-panning so as to prepare a target-specific non-antibody protein capable of optimally binding with the particular site of the predetermined target protein. Furthermore, they have prepared a non-antibody protein targeting the EGFR (Epidermal Growth Factor Receptor) domain 2 as a target for anticancer treatment, and examined its binding ability with the target, thereby completing the present invention.

SUMMARY OF THE INVENTION

An object of the present invention is to provide a method for preparing a target-specific non-antibody protein comprising the steps of: (a) selecting non-antibody proteins having a structural complementarity with the target site of a target protein in a non-antibody protein library; (b) calculating a binding energy of the selected non-antibody protein and the target protein; (c) selecting a non-antibody protein having a favorable binding energy among the selected non-antibody proteins; (d) selecting amino acid residues having a high binding energy among the interfacial amino acid residues of the selected non-antibody protein and the target protein; and (e) substituting the amino acid residues selected in step (d) with the amino acid residues having a low binding energy.

Another object of the present invention is to provide a target-specific non-antibody protein that specifically binds to the EGFR domain 2.

Still another object of the present invention is to provide a nucleic acid encoding the target-specific non-antibody protein that specifically binds to the EGFR domain 2, a vector comprising the nucleic acid, or a transformant transformed with the vector.

Still another object of the present invention is to provide a cancer therapeutic composition, comprising the target-specific non-antibody protein that specifically binds to the EGFR domain 2.

BRIEF DESCRIPTION OF THE DRAWINGS

FIG. 2 shows an amino acid sequence of EGFR (SEQ ID NO.:1), in which the underlined amino acids are 166 to 309 amino acids of EGFR domain 2, and 28 amino acid residues in the box are selected as interfacial residue candidates;

FIG. 6 shows an amino acid sequence (left, SEQ ID NO:2) and a DNA sequence (right, SEQ ID NO:6) of the wild type scaffold before mutation by randomization of the 1OZJ scaffold, in which the underlined sequences are the unfavorable residues to be mutated;

FIG. 7 shows an amino acid sequence (left, SEQ ID NO:3) and a DNA sequence (right SEQ ID NO:7) of clone 6 of the 1OZJ scaffold, in which the underlined sequences are the unfavorable residues to be mutated;

FIG. 8 shows an amino acid sequence (left, SEQ ID NO:4) and a DNA sequence (right SEQ ID NO:8) of clone 7 of the 1OZJ scaffold, in which the underlined sequences are the unfavorable residues to be mutated; and FIG. 9 shows an amino acid sequence (left, SEQ ID NO:5) and a DNA sequence (right SEQ ID NO:9) of clone 9 of the 1OZJ scaffold, in which the underlined sequences are the unfavorable residues to be mutated.

DETAILED DESCRIPTION OF THE PREFERRED EMBODIMENTS

In order to achieve the above objects, one embodiment of the present invention relates to a method for preparing a target-specific non-antibody protein comprising the steps of: (a) selecting non-antibody proteins having a structural complementarity with the target site of a target protein in a non-antibody protein library; (b) calculating a binding energy of the selected non-antibody protein and the target protein; (c) selecting a non-antibody protein having a favorable binding energy among the selected non-antibody proteins; (d) selecting amino acid residues having a high binding energy among the interfacial amino acid residues of the selected non-antibody protein and the target protein; and (e) substituting the amino acid residues selected in step (d) with the amino acid residues having a low binding energy.

Figure 1:
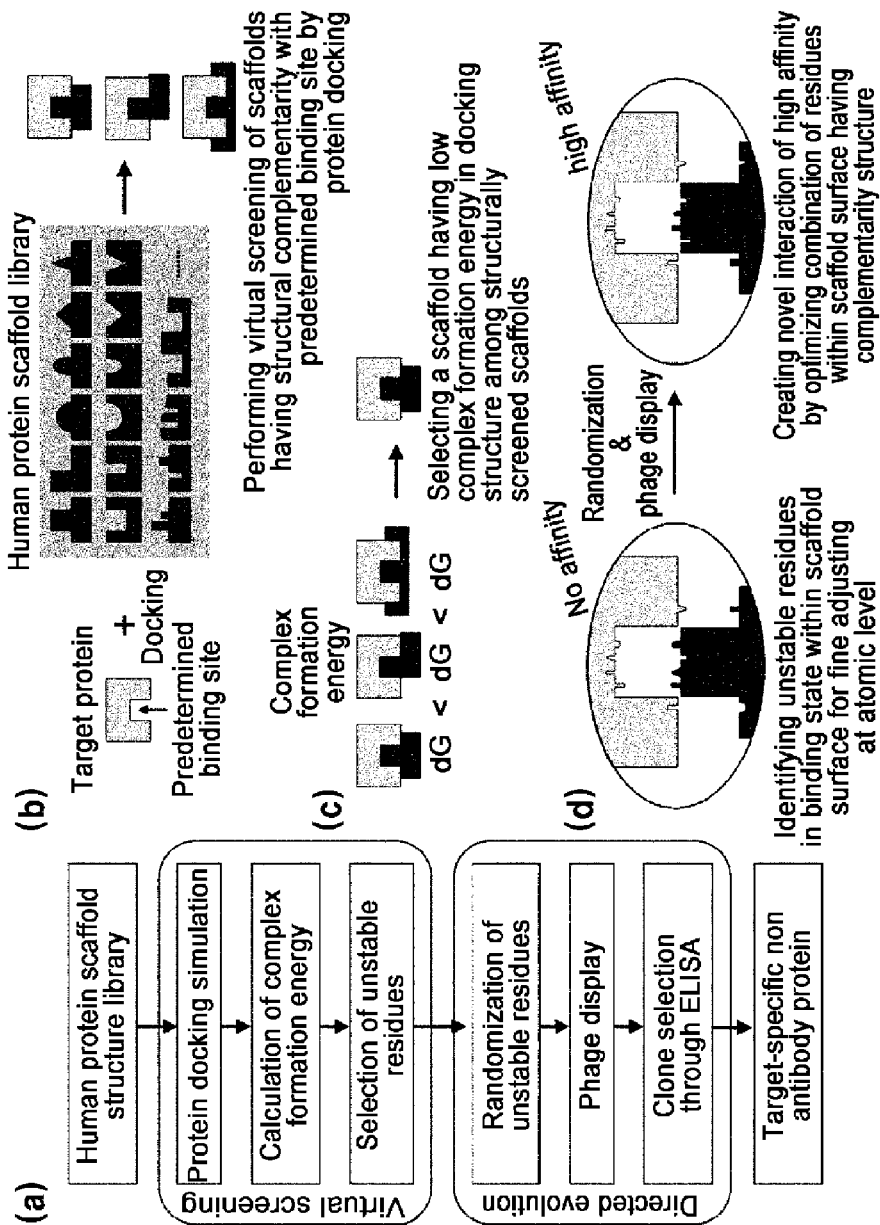
FIG. 1 is an overview of PELEX (Protein Engineering with Laboratory Evolution & Extensive Computation) method for design of the target-specific scaffold of the present invention, in which (a) is a flow chart of two-step PELEX, including the steps of performing virtual screening consisting of docking simulation and complex formation energy calculation based on the human protein scaffold library; and performing directed evolution for optimization of binding affinity between the screen scaffold and the predetermined binding site, (b) is a view of selecting protein scaffolds having a complement shape with the predetermined binding site of a target protein based on the human protein scaffold library and docking simulation, in which a large scale of the protein scaffold library includes all of the known human protein structures, (c) is a view of selecting scaffolds that exhibit favorable binding energy for further optimization by directed evolution, after calculation of complex formation energy using the screened docking structures, and (d) is a view of performing directed evolution by sequence randomization and phage display for refinement of the target-specific scaffolds, in which the unfavorable interfacial residues are randomized for affinity optimization of the target and the scaffold.

An overview of the method for preparing a target-specific non-antibody protein of the present invention is shown in FIG. 1a. The present inventors designated the present method for preparing a target-specific non-antibody protein, which includes the steps of performing virtual screening by docking simulation developed by the present inventors and calculation of binding energy; and performing directed evolution by randomization of residues through phage display and biopanning, as PELEX (Protein Engineering with Laboratory Evolution & Extensive Computation).

As used herein, the term "non-antibody protein" is a protein having a molecular weight of 10 to 40 kDa, which is 1/10 lower than those of the existing therapeutic antibodies, and is a non-antibody protein that easily penetrates into a target tissue and can be mass-produced in bacteria or the like. It also means a protein capable of treating various diseases such as cancer and autoimmune diseases or capable of preventing progression of the diseases by selectively recognizing particular target molecules and strongly binding thereto so as to inhibit activity of the target molecules. Herein, the "non-antibody protein" can be used interchangeably with "scaffold", "scaffold protein", or "binding protein".

As used herein, the term "non-antibody protein library" means a collection of protein scaffolds consisting of all protein structures in the nature, of which tertiary structures have been revealed by human, and this collection may be prepared to exist in the database. For the preparation of the non-antibody protein library, database including all tertiary structures of the human proteins such as PDB (Protein Data Bank) and SCOP (Structural Classification of Protein) may be used, but is not limited thereto. The various other databases including all tertiary structures of the human proteins are also used to select proteins for the preparation of the non-antibody protein library. These databases are classified into a plurality of groups according to each tertiary structure of the human proteins. The specific preparation method of the non-antibody protein library is as follows. First, in order to facilitate tissue penetration, proteins having a limited molecular weight of 10 to 40 kDa are only selected from human proteins. In this connection, representative five or fewer proteins having a molecular weight ranging from 10 to 40 kDa are selected from each structural class of the human proteins. Thus, all types of the human proteins are included and the size of electric library is also reduced, thereby improving search speed. Subsequently, to rule out proteins other than non-antibody proteins from the human proteins, the step of removing membrane proteins and antibody proteins may be included. The databases of proteins with known structures were used without limitation so as to rule out membrane proteins and antibody proteins, and for example, a keyword search may be performed using a database such as PDBTM (Protein Data Bank of Transmembrane Proteins). Thereafter, to avoid random binding, the step of selecting proteins that are known only to have 10 or fewer interactions may be included. Information regarding such interactions is also obtained from various databases providing information on protein-protein interactions. For example, the number of protein-protein interactions can be calculated using HPRD (Human Protein Reference Database). To rule out proteins having numerous interactions, such as homotetramer and homohexamer, the step of sorting proteins capable of forming any one or more monomer, homodimer, and homotrimer may be included. The known databases, generally used to determine binding between proteins, may be used without limitation, and for example, SWISS-PROT database can be used. The non-antibody protein library prepared by all of the above steps may include 1000 to 2000 non-antibody proteins with known structures. According to one embodiment of the present invention, a non-antibody protein library consisting of 1261 non-antibody soluble proteins with a low molecular weight and a low risk of random binding was prepared, and virtual screening such as docking simulation was performed on the basis of this library.

Preferably, step of (a) selecting non-antibody proteins having a structural complementarity with the target site d of a target protein in a non-antibody protein library; and (b) calculating a binding energy of the selected non-antibody protein and the target protein may be performed sequentially or at the same time.

As used herein, the term "target protein" means a desired protein binding with the non-antibody protein, and it may vary according to a desired application via binding of the non-antibody protein. It may be selected from cancer-causing proteins, immune disease-causing proteins, and foreign proteins infected without limitation, and for example, EGFR (Epidermal Growth Factor Receptor).

As used herein, the term "target site" is a region in the tertiary structure of the target protein, which directly or indirectly participates in pathological protein interactions and bindings, and the non-antibody protein strongly binds to the corresponding region so as to prevent malicious protein interactions. An example thereof may be EGFR domain 2. Further, the binding site of the target protein, which binds with the non-antibody protein of the present invention, may have various surfaces such as concave surface, and thus the preparation of the non-antibody protein is not limited to the tertiary structure of the target protein binding therewith.

As used herein, the term "EGFR (Epidermal Growth Factor Receptor)" is a representative growth factor receptor, and overexpressed on the surface of various cancer cells such as breast cancer, lung cancer, colorectal cancer, renal cancer, gallbladder cancer, head and neck cancer, ovarian cancer, prostate cancer, cervical cancer and gastric cancer. It means an EGF receptor that is activated by binding of the growth factor EGF so as to play a significant role in cancer cell proliferation, invasion, angiogenesis or metastasis. Until recently, a variety of EGFR-targeting agents that inhibit EGFR to selectively attack cancer cells have been actively studied, but there is little study of targeting the EGFR domain 2 used as a target in the present invention.

Figure 3:
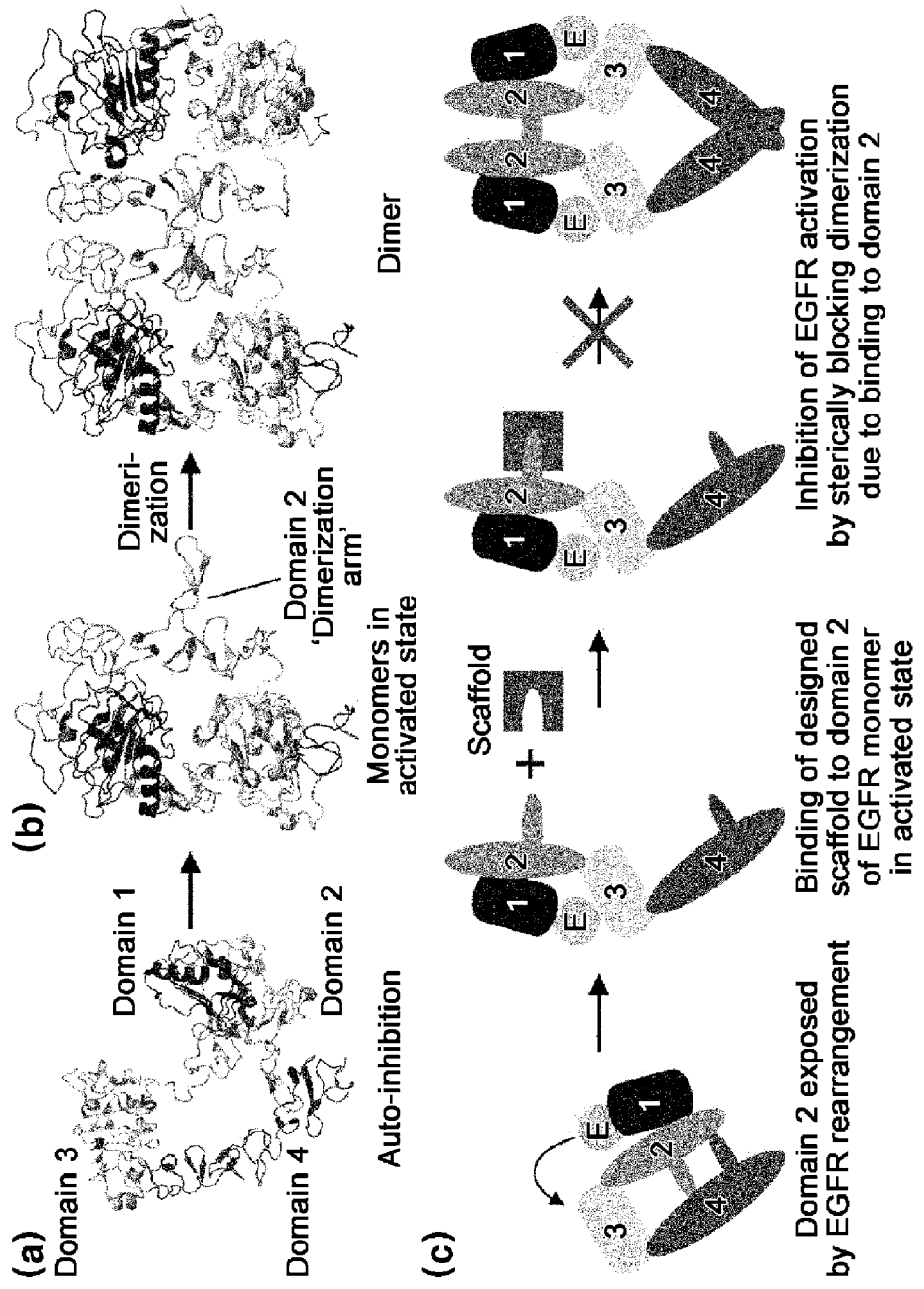
FIG. 3 shows an EGFR activation mechanism and a scaffold activation mechanism designed for the inhibition of EGFR activation, in which (a) shows EGFR inactivated by intramolecular interaction between domain 2 and domain 4 in an auto-inhibition state, and dimerization arm of domain 2 is occluded, (b) shows that EGF binding removes the intramolecular interaction between domain 2 and domain 4, and promotes a large domain rearrangement that exposes domain 2 so as to activate EGFR, and EGFR molecules form a homodimer by interactions between each "dimerization arm" of domain 2, and (c) shows a mechanism of inhibiting the EGFR activity by binding the designed scaffold to the EGFR domain 2 to prevent homodimer formation, in which the binder protein recognizes only the activated EGFR, but does not recognize the auto-inhibited EGFR.

EGFR consists of four domains. It binds with the ligand EGF to cause a conformational change, and the exposed domain 2 mediates homodimer formation, leading to EGFR activation. Therefore, the non-antibody protein strongly binding with the EGFR domain 2 used as a target of the present invention specifically binds to the domain 2 that is exposed by binding of the ligand EGF, so as to prevent homodimer formation, thereby specifically inhibiting the EGFR activity (FIG. 3). Briefly, since the non-antibody protein selectively inhibits the activated EGFR only, it selectively attacks cancer cells other than normal cells and thus, functions as a cancer therapeutic agent.

Step (a) of selecting non-antibody proteins having a structural complementarity with the target protein in the non-antibody protein library is a step of examining whether a plurality of non-antibody proteins or scaffolds in the prepared non-antibody protein library have a structural complementarity with the target protein using a super computer, which can be conducted by performing virtual binding using docking simulation. This step is intended to prepare various docking complexes through virtual binding of the target with diverse scaffolds in the scaffold library, and the docking simulation may be performed by known programs without limitations, such as ZDOCK, PIPER, ClusPro, ICM-DISCO, Rosetta-Dock, PatchDock, and MolFit. According to one embodiment of the present invention, PatchDock was used to select non-antibody proteins having a structural complementarity. There are numerous methods of binding a single target with a single non-antibody protein by structural complementarity, and the PatchDock program is used to rank the docked structures, based on complementarity. At this time, the docking structures ranked in the top 10 are selected from various docking structures of each non-antibody protein, and used in the next analysis step. Preferably, the docking simulation step is to select non-antibody proteins that bind with a predetermined number or more of target amino acid residues of the target protein. More preferably, if the target site of the target protein is the EGFR domain 2, the number of the interfacial residues of the target and the non-antibody protein may be 28 and the predetermined number is 10. That is, when 10 or more of the 28 interfacial residues participate in the binding, the scaffolds of the docking structures are regarded as a favorable structure for binding with the EGFR domain 2, and thus the non-antibody proteins forming the docking structures can be selected. The number of interfacial residues may vary depending on the type of target protein or target site.

Step (b) is a step of calculating a binding energy of the non-antibody protein selected in step (a) and the target protein, and a step of selecting non-antibody proteins which are able to bind with the desired region of the target protein at the predetermined level or higher, based on the results of the docking simulation. In this regard, when the number of the target residues participating in the binding is more than the predetermined number, the binding may occur favorably.

The binding energy of the non-antibody protein and the target is calculated according to the following Equation 1. The binding energy may be calculated by a variety of known programs, but is not limited to, for example, EGAD, RossetaDesign or the like. According to one embodiment of the present invention, EGAD program was used to calculate the binding energy.

$$\Delta G\text{binding} = \Delta G\text{complex} - \Delta g\text{free} \quad \text{[Equation 1]}$$

The binding energy ($G_{binding}$) is the energy that is required for binding of the target protein and the non-antibody protein, and defined as the energy difference between the energy ($G_{complex}$) of the complex of the target protein and the non-antibody protein and each energy ($G_{free}$) of the target protein and the non-antibody protein before the binding. The non-antibody proteins are arranged in order from lowest to highest binding energy.

Step (c) is the step of selecting a non-antibody protein having a favorable binding energy from the selected non-antibody proteins. As the binding energy is lower, the binding of the target and the non-antibody protein occurs favorably, and thus the possibility of stronger and more specific binding is increased. In this regard, it is preferable that the desired number is predetermined, and the non-antibody proteins are arranged only as many as the predetermined number.

Step (d) is a step of selecting amino acid residues having a high binding energy among the interfacial amino acid residues of the selected non-antibody protein and the target protein, and the binding energy of each interfacial amino acid residue is calculated to examine the energy contribution of each residue. The residues having an unfavorable binding energy are selected for further randomization. For the convenience of randomization, the scaffolds having a large number of unfavorable residues can be excluded by comparison of the top-ranked scaffolds. According to one embodiment of the present invention, 1OZJ was selected as a scaffold having a high structural complementarity and a favorable binding energy among the selected non-antibody protein-EGFR domain 2 docking complexes, and the binding energy of each residue participating in the binding of the selected 1OZJ was calculated. As a result, five interfacial residues of 44Lys, 107Glu, 110Glu, 114Asn, and 118Asp that were found to have a high binding energy were selected as unfavorable residues (FIG. 4*c*, Table 2).

Step (e) is a step of substituting the unfavorable amino acid residues selected in step (d) with the amino acid residues having a low binding energy, and performed by directed evolution. Namely, the unfavorable interfacial residues of the target protein and the non-antibody protein, which have a high binding energy to impede the binding, are substituted with the amino acid residues having a low binding energy, thereby leading to favorable binding. The substitution of amino acid residues may be performed by the known molecular biological method without limitation, preferably, phage display and bio-panning. According to one embodiment of the present invention, the binding energy of each residue participating in the binding of the selected scaffold 1OZJ was calculated. For the substitution of five amino acid residues of 44Lys, 107Glu, 110Glu, 114Asn, and 118As that were found to have a high binding energy, a phage display random library was constructed and 5 rounds of bio-panning were performed to identify stronger clones than the wild type 1OZJ scaffold by phage ELISA (FIG. 5).

The present invention prepared a human scaffold library consisting of 1,261 non-antibody soluble proteins with a molecular weight of 10 to 40 kDa and a low risk of random binding among all the known human proteins. Then, in order to screen scaffolds complementary to EGFR domain 2, a PatchDock program was used to perform a large scale of docking simulation, thereby selecting the top ranked 10 docking models. In this connection, when 10 or more of 28 residues of EGFR domain 2 participate in the binding, the scaffolds are regarded as a stable structure. As a result, protein scaffolds having complement shape with target binding site of the EGFR domain 2 were found. The energy contribution of each residue of the selected scaffolds was calculated using EGAD so as to select the scaffold 1OZJ having the most favorable complex formation energy and five interfacial residues having an unfavorable binding energy (Table 1 and FIG. 4). Thereafter, through phage display library construction and bio-panning, substitution of the five residues with the residues having a favorable binding energy was performed, and then binding with the EGFR was examined by phage ELISA so as to select 15 stronger clones (Table 2 and FIG. 5). Among the clones, the strongest 6, 7 and 9 clones were selected, and sequence analysis was performed to prepare a strong target-specific non-antibody protein enriched by substitution with the desired sequences (FIGS. 7 to 9).

Another embodiment of the present invention relates to a target-specific non-antibody protein that specifically binds to the EGFR domain 2.

The target-specific non-antibody protein that specifically binds to the EGFR domain 2 is the same as the above described, and may be preferably prepared by the method for preparing a target-specific non-antibody protein. Preferably, the target-specific non-antibody protein that specifically binds to the EGFR domain 2 may have an amino acid sequence of SEQ ID NO. 3, 4 or 5. According to one embodiment of the present invention, a phage ELISA of 1OZJ that is selected as the target-specific non-antibody protein specifically binding to the EGFR domain 2 was performed, and the resulting clones 6, 7 and 9 that have an increased binding ability to EGFR were subjected to amino acid sequence analysis. Consequently, they were found to have the sequences of SEQ ID NOS. 3, 4 and 5, respectively (Table 2, FIGS. 5 and 7 to 9).

Still another embodiment of the present invention relates to a nucleic acid encoding the target-specific non-antibody protein that specifically binds to the EGFR domain 2. Preferably, the nucleic acid may have the nucleic acid sequence of SEQ ID NO. 7, 8 or 9. According to one embodiment of the present invention, a phage ELISA of 1OZJ that is selected as the target-specific non-antibody protein specifically binding to the EGFR domain 2 was performed, and the resulting clones 6, 7 and 9 that have an increased binding ability to EGFR were subjected to nucleic acid sequence analysis. Consequently, their nucleic acids were found to have the sequences of SEQ ID NOS. 7, 8 and 9, respectively (Table 2, FIGS. 5 and 7 to 9).

Still another embodiment of the present invention relates to a vector including the nucleic acid encoding the target-specific non-antibody protein that specifically binds to the EGFR domain 2. Examples of the vector of the present invention include a plasmid vector, a cosmid vector, a bacteriophage vector, and a virus vector, but are not limited thereto. Examples of the suitable expression vector include expression regulatory elements such as a promoter, an operator, an initiation codon, a termination codon, a polyadenylation signal, and an enhancer, as well as a signal sequence for membrane targeting or secretion, or a leader sequence. The promoter of the vector may be constitutive or inducible. Further, the expression vector includes a selective marker for selection of a host cell having the vector.

Still another embodiment of the present invention relates to a transformant that is transformed with the vector including the nucleic acid encoding the target-specific non-antibody protein that specifically binds to the EGFR domain 2.

A transformation method includes any method for introducing the nucleic acid into an organism, a cell, a tissue or an organ, and can be performed by employing the preferable standard technology according to the host cell as known in the art. Examples thereof include an electroporation, a cytoplasmic fusion, calcium phosphate ($CaPO_4$) precipitation, calcium chloride ($CaCl_2$) precipitation, agitation with silicon carbide fiber, an agrobacterium mediated transformation, PEG, dextran sulfate, and lipofectamine, but are not limited thereto. The amount of expression and modification are different according to the host cell, and the most preferable host cell is selected and used according to its purpose. Examples of the host cell include prokaryotic cells such as *Escherichia coli, Bacillus subtilis, Streptomyces, Pseudomonas, Prometeus mirabilis* and *Staphylococcus*, but are not limited thereto. Further, lower eukaryotic cells such as fungus (e.g., *Aspergillis*) and yeast (e.g., *Pichia pastoris, Saccharomyces cerevisiae, Schizosaccharomyces, Neurospora crassa*), and cells derived from higher eukaryotic cells including an insect cell, a plant cell, and a mammalian cell may be used as the host cell.

Still another embodiment of the present invention relates to a therapeutic or prophylatic composition for cancer, including the target-specific non-antibody protein that specifically binds to the EGFR domain 2.

The therapeutic or prophylatic composition for cancer of the present invention is applicable to all types of cancer caused by EGFR activation, and applicable to any animal having the cancer. The animal includes livestock such as cattle, pigs, sheep, horses, dogs, and cats, as well as humans and primates without limitation.

As used herein, the term "prevention" means all of the actions in which the occurrence of cancer is restrained or retarded by the administration of the composition including a non-antibody protein of the present invention. The term "treatment" means all of the actions in which cancer has taken a turn for the better or been modified favorably by the administration of the composition including a non-antibody protein of the present invention. If the EGFR domain 2-specific non-antibody protein is used for a therapeutic composition, it is directly coupled with (e.g., covalent bond) or indirectly coupled with the existing therapeutic agent via a linker or the like, so as to be administered into the body in a non-antibody protein-therapeutic agent complex form for the prevention or treatment of cancer. The therapeutic agents to be used include chemotherapeutic agents, immunotherapeutic agents, cytokines, chemokines, antiviral agents, biological agents, enzyme inhibitors or the like. The cancer therapeutic agent including the EGFR domain 2-specific non-antibody protein of the present invention may further include a pharmaceutically acceptable carrier, and may be formulated together with the carrier. As used herein, the term "pharmaceutically acceptable carrier" refers to a carrier or diluent that does not cause damage to the biological activity and properties of the active ingredient. For liquid formulation, the pharmaceutically acceptable carriers should be sterilized and suitable to living bodies. For example, the pharmaceutically acceptable carriers may include a saline solution, sterilized water, a Ringer's solution, a buffered saline solution, an albumin injection solution, a dextrose solution, a malto dextrin solution, glycerol, ethanol, or the mixture of one or more of the above ingredients. If necessary, other common additives can be added, such as antioxidants, buffers, bacteriostatic agents or the like. Also, diluting agents, dispersing agents, surfactants, binders or lubricants may be further added in order to formulate the composition to injection formulations such as an aqueous solution, a suspension, and an emulsion, pills, capsules, granules, or tablets.

The anticancer composition including the EGFR domain 2-specific non-antibody protein and pharmaceutically acceptable carriers is applicable to any formulation including the anticancer composition as an active ingredient, and may be formulated into oral or parenteral formulations. The pharmaceutical formulations of the present invention may include those suitable for oral, rectal, nasal, topical (including buccal and sublingual), transdermal, vaginal, or parenteral (including intramuscular, subcutaneous, and intravenous) administration or a form suitable for administration by inhalation or insufflation.

The formulations for oral administration including the composition of the present invention as an active ingredient include tablet, troche, lozenge, water-soluble or oil suspension, powder or granulate, emulsion, hard or soft capsule, syrup or elixir, etc. In order to prepare the formulation in the form of tablet and capsule, the composition may further include binder such as lactose, saccharose, sorbitol, mannitol, starch, amylopectin, cellulose or gelatin; excipient such as dicalcium phosphate; disintegrant such as corn starch or potato starch; and lubricant such as magnesium stearate, calcium stearate, sodium stearyl fumarate or polyethylene glycol wax. For capsules, a liquid carrier, such as a lipid, may be further used in addition to the above-mentioned compounds.

The formulations for parenteral administration including the composition of the present invention as an active ingredient may be formulated into injections for subcutaneous, intravenous or intramuscular routes, suppositories, or sprays inhalable via the respiratory tract, such as aerosols. Injection preparations may be obtained by dissolving or suspending the composition of the present invention, together with a stabilizer or a buffer, in water and packaging the solution or suspension in ampules or vial units. Suppositories are typically made of a suppository base, such as cocoa butter or another glyceride, or a therapeutic laxative. For sprays, such as aerosol, a propellant for spraying a water-dispersed concentrate or wetting powder may be used in combination with an additive.

Hereinafter, the present invention will be described in more detail with reference to the following Examples. However, these Examples are for illustrative purposes only, and the invention is not intended to be limited by these Examples.

Example 1

Construction of Structurally Defined Human Scaffold Library

In order to construct a human protein scaffold library including almost every known human protein, 5 representative structures were retrieved from each of a plurality of groups classified according to 3D protein structures of human proteins in SCOP (Structural Classification of Proteins) database. In order to facilitate tissue penetration, five or fewer representative proteins having a limited molecular weight of 10 to 40 kDa were selected so as to include all types of human proteins and to reduce a size of the library. Then, the present inventors ruled out membrane protein structures using annotation in PDBTM database and antibodies by keyword search. Thereafter, to avoid random binding, proteins having 10 or fewer known interactions were only selected. The number of protein-protein interactions was calculated using HPRD (Human Protein Reference Database). Based on the 'SUBNIT' section of SWISS-PROT database, homomultimers having numerous interactions, such as homotetramers and homohexamers, were ruled out, and proteins forming monomers, homodimers, and homotrimers were selected.

As a result, a human protein scaffold library consisting of 1261 non-antibody soluble proteins with a low molecular weight and a low risk of random binding was constructed.

Example 2

Structure-Based Virtual Screening

In order to screen scaffolds having a complement shape with the EGFR domain 2 based on the human protein scaffold library constructed in Example 1, virtual screening by massive docking simulation with EGFR was performed (FIG. 1b). The method is as follows. The original purpose of protein docking simulation is to predict existing protein-protein interactions, but in the present invention it is applied to find structural complementarity between two proteins for creating novel protein-protein interactions.

To screen scaffolds having a complementary structure with the EGFR domain 2, docking simulation between the A chain of human EGFR extracellular region (PDB id: 1IVO, Ogiso H et. al, Cell. September 20; 110(6):775-87, 2002) and each scaffold in the library was performed using Patch Dock program (Schneidman-Duhovny, D. et al. Proteins 52, 107-112 (2003), Schneidman-Duhovny, D. et al. Nucleic Acids Res 33, W363-367 (2005)). Next, top ranked 10 docking models were generated from the scaffold-EGFR docking results, and binding patterns of the models were analyzed to identify the residues of EGFR involved in the complex formation and to find a docking structure of EGFR domain 2. 28 interfacial residues of the EGFR domain 2 as a target site were predetermined. When 10 or more of the 28 interfacial residues participate in the complex formation, the scaffolds of the docking complexes are regarded as a favorable structure for binding with the EGFR domain 2 (166 to 309 sequences in EGFR amino acid sequences of SEQ ID NO. 1, FIG. 2): 229, 230, 239, 242, 244, 245, 246, 248, 249, 250, 251, 252, 253, 262, 263, 264, 265, 275, 278, 279, 280, 282, 283, 284, 285, 286, 303, 304 (28 predetermined amino acid sequences in EGFR amino acid sequences of SEQ ID NO. 1, FIG. 2).

In the present invention, the residues having a change in SASA (solvent accessible surface area) greater than 1 Å$^2$ upon formation of a docking complex between two chains were regarded as those involved in the complex formation. SASA of each residue was calculated using Naccess (http://www.bioinf.manchester.ac.kr), thereby identifying the particular residues involved in the complex formation.

As a result, protein scaffolds having complement shape with target binding site of the EGFR domain 2 were found.

Example 3

Figure 4:
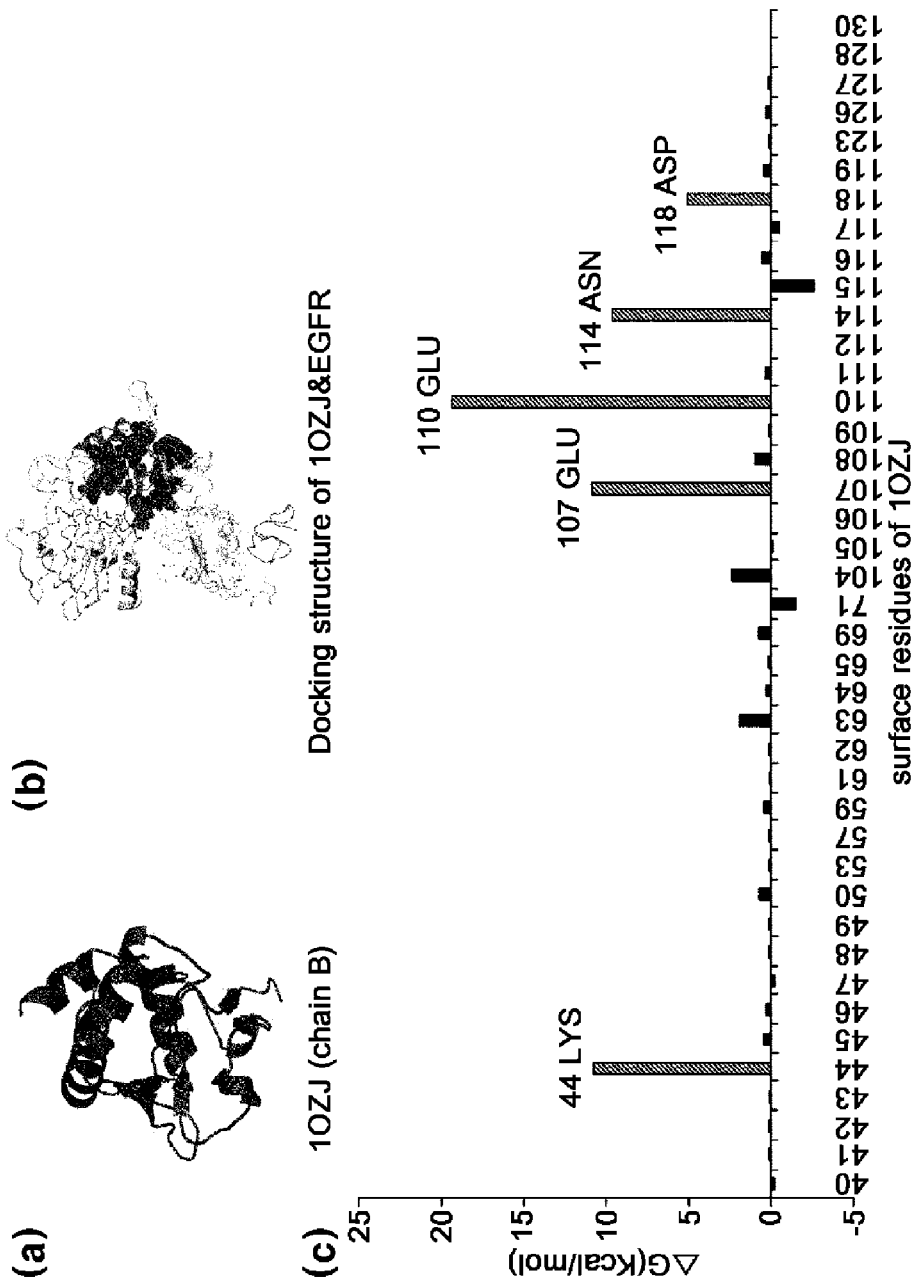
FIG. 4 shows the structure and energy of 1OZJ, in which (a) illustrates the structure of 1OZJ (chain B), (b) illustrates the docking structure of 1OZJ-EGFR, in which the deep-colored chain indicates the scaffold, the light-colored chains indicate domain 1, 2, 3 and 4 of EGFR, and the interfacial residues of EGFR and the scaffold are displayed by sphere (the scaffold structure of (a) is displayed in the same direction as that of (b)), and (c) shows the energy contribution of interfacial residues of 1OZJ for complex formation with EGFR, in which unfavorable residues selected for further refinement by direct evolution are indicated by oblique bars, and they are amino acid residues to be mutated by further randomization.

Calculation of Complex Formation Energy and Selection of Energetically Favorable Protein Scaffolds Among the selected scaffold-EGFR docking complexes involved in the binding of the EGFR domain 2, a few scaffolds exhibiting most favorable complex formation energy were screened for further refinement (FIG. 1*c*).

Complex formation energy of the scaffold-EGFR docking complexes and the energy contribution of each interfacial residue of the scaffolds were calculated using EGAD (http://egad.berkeley.edu/EGAD_manual/index.html). The docking structures generated by PatchDock were used as a template, and complex_formation_energy was entered as a command in the JOBTYPE field so as to calculate the binding energy. Default values were used for all other options. As a result, a pseudo_DELTA_G complex formation value was obtained as complex formation energy, and dG values of the interfacial residues, displayed as level_1, were collected to select unfavorable residues. At this time, the residues of level_2 indirectly involved in the binding were excluded. During this process, two additional criteria were considered, besides to the favorable energy. First, the scaffolds having no suitable structures are filtered out by manual inspection. Second, scaffolds of which less number of unfavorable residues is well clustered in primary sequence were preferred due to the convenience of random sequence library construction for directed evolution.

The binding energy was calculated using the following Equation 1.

$$\Delta G\text{binding}=\Delta G\text{complex}-\Delta g\text{free} \quad \text{[Equation 1]}$$

The binding energy ($G_{binding}$) is the energy that is required for the binding of the target protein and the non-antibody binder protein, and the energy difference between the energy ($G_{complex}$) of the complex of the target protein and the non-antibody protein and each energy ($G_{free}$) of the target protein and the non-antibody protein before the binding was calculated to determine the stability of complex formation.

As a result, B chain (FIG. 4*a*) of 1OZJ (Crystal structure of Smad3-MH1) was selected as a scaffold having the most favorable complex formation energy (Table 1). The complex formation energy of 1OZJ with EGFR was calculated by docking model (FIG. 4*b*). The scaffold is indicated by deep color, and a structure of the scaffold is shown in FIG. 4*a* in the same way. The interfacial residues of the scaffold with EGFR are displayed by sphere.

TABLE 1

| PDB id | chain | PatchDock rank | ddG (kcal/mol) |
|---|---|---|---|
| 2A5E | — | 9 | 36.86 |
| 1KZY | D | 4 | 62.75 |
| 1ZOP | B | 8 | 76.26 |
| 1OZJ | B | 9 | 84.69 |
| 4FAP | B | 1 | 86.45 |
| 1AUT | L | 9 | 88.62 |
| 1RK9 | A | 10 | 94.61 |
| 1XMJ | A | 4 | 110.12 |
| 1SI3 | A | 9 | 111.94 |
| 1SI3 | A | 1 | 114.67 |

Then, by examining the energy contribution of each interfacial residue of selected scaffolds, unfavorable amino acid residues for complex formation were selected for sequence randomization. FIG. 4c is the result showing energy contribution of each interfacial residue of 1OZJ.

As a result, five residues of 1OZJ indicated by oblique bars were selected for sequence randomization (44Lys, 107Glu, 110Glu, 114Asn, 118Asp, FIG. 4c).

Example 4

Construction of Random Library

DNA (SEQ ID NO. 6, FIG. 6) of EGFR-binding scaffold (1OZJ) selected in Example 3 was synthesized by Genscript (Piscataway, N.J.), and NNK primers designed for randomization of the particular binding region were used to perform randomization. The randomized scaffold was cleaved using SfiI (Roche, Indianapolis, Ind.), ligated into a phagemid vector pComb3X, and transformed into the electrocompetent ER2738 (New England Biolabs, Beverly, Mass.) to construct a random library.

As a result, the selected 5 unfavorable interfacial residues of 1OZJ are fully randomized by construction of randomization library. A total of $4*10^8$ combinations of selected interfacial residues were generated. Then, strong binder proteins were screened among the mutants based on the following phage display.

Example 5

Bio-Panning, Phage Display and Phage ELISA

<5-1> Bio-Panning and Phage Display

To enrich the EGFR-specific binder protein, 5 rounds of bio-panning were performed as an affinity selection technology.

The present inventors coated and blocked Dynabead M-270 Epoxy (Dynal, Invitrogen, Carlsbad, Calif.) in accordance with manufacturer's instructions. $5 \times 10^6$ Dynabeads were coated with 1.5 µg EGFR (Sigma, St. Louis, Mo.) in PBS (137 mM sodium chloride, 10 mM phosphate, 2.7 mM potassium chloride, ph 7.4) as a stock solution (1 ml/mg) for each round of panning. EGFR-coated Dynabeads were cultured together with 500 µl of the randomized phage library in a room temperature rotator for 2 hrs. To remove unbound phages, Dynabeads were washed with 0.05% Tween 20-containing PBS (v/v) once after a first round of bio-panning, three times after second and third rounds of bio-panning, and five times after two remaining rounds of panning. The phages binding to the EGFR-coated Dynabead were eluted using 30 µl of 0.1 M glycine-HCl (pH 2.2) twice and neutralized by addition of 2 M Tris-HCl (pH 9.1). Fresh cultured ER2738 was infected with the eluted phages, and cultured overnight for next bio-panning.

<5-2> Phage ELISA

Individual colonies were randomly selected from the output titration plate of the last round, and inoculated in 1 ml of super broth (3% tryptone, 2% yeast extract, 1% 3-[N-Morpholino] propanesulfonic acid [MOPS], pH 7.0). after overnight incubation at 37° C., the supernatant was used for phage ELISA (enzyme-linked immunosorbant assay). microtitration plate wells were coated with 4 µg/ml EGFR-containing PBS at 4° C. for one night, and blocked with 3% BSA-containing PBS at 37° C. for 1 hour. The plate was cultured with the phage-containing supernatant at 37° C. for 2 hours, and washed with 0.05% Tween-20-containing PBS (PBST) three times. Thereafter, HRP (horseradish peroxidase)-conjugated anti-M13 antibody (Sigma) diluted in a blocking buffer solution (1:2000) was added thereto and cultured at 37° C. for 1 hour. 50 µl of TMB substrate solution (Pierce, Rockford, Ill.) was added to each well, and OD was measured at 650 nm.

Figure 5:
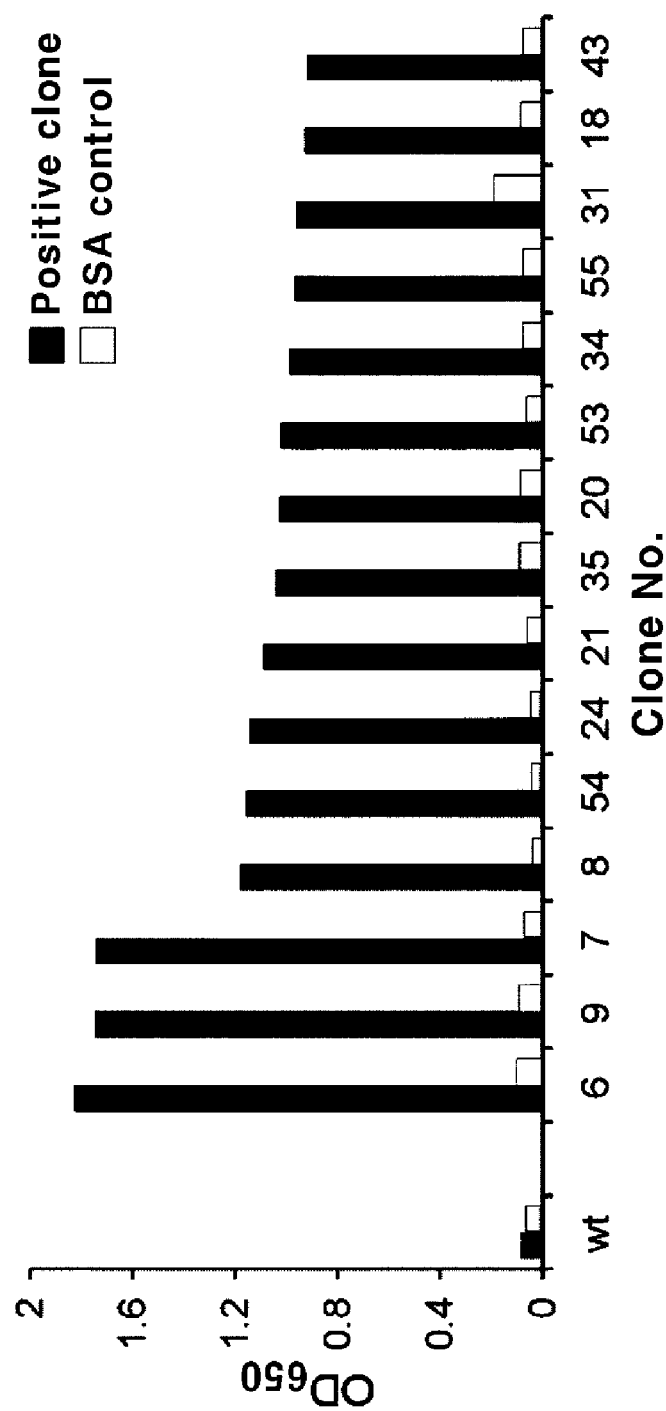
FIG. 5 is the results of ELISA showing the binding affinity after mutation of the unfavorable residues of 1OZJ, in which a horizontal axis represents Clone No., and a vertical axis represents optical density obtained from the ELISA analysis, and the results of sequence randomization of the 1OZJ clones are shown in Table 2.

After panning, the clones from the 1OZJ scaffold were found to have a greatly increased binding ability with EGFR (FIG. 5). The affinity of the wild type 1OZJ to EGFR were not shown, but after randomization of the five amino acids selected in Example 3, 15 or more of the 1OZJ mutant clones showed a strong binding ability with EGFR (FIG. 5 and Table 2). Amino acid and DNA sequences of the strongest clones 6, 7 and 9 were analyzed by a molecular biological method. As a result, clone 6 was found to have the amino acid sequence of SEQ ID NO. 3 and the DNA sequence of SEQ ID NO. 7 (FIG. 7). Clone 7 was found to have the amino acid sequence of SEQ ID NO. 4 and the DNA sequence of SEQ ID NO. 9 (FIG. 8). Clone 9 was found to have the amino acid sequence of SEQ ID NO. 5 and the DNA sequence of SEQ ID NO. 8 (FIG. 9).

TABLE 2

| Clone | 44 | 107 | 110 | 114 | 118 | OD at 650 nm |
|---|---|---|---|---|---|---|
| WT | K | E | E | N | D | 0.086 |
| 6 | S | G | S | N | L | 1.826 |
| 9 | A | Q | I | L | P | 1.748 |
| 7 | L | A | A | M | C | 1.741 |
| 8 | G | P | N | T | P | 1.18 |
| 54 | C | I | D | P | R | 1.156 |
| 24 | S | A | D | V | E | 1.144 |
| 21 | T | L | A | A | M | 1.089 |
| 35 | T | L | A | A | M | 1.041 |
| 20 | S | T | T | Q | G | 1.028 |
| 53 | A | S | S | S | I | 1.02 |
| 34 | S | T | T | Q | G | 0.987 |
| 55 | I | K | R | P | D | 0.964 |
| 31 | G | H | P | K | W | 0.959 |
| 18 | S | A | D | V | E | 0.927 |
| 43 | R | H | N | G | A | 0.919 |

The results of Table 2 and FIG. 5 suggest that a new binding is truly generated between the scaffold protein and EGFR having no relevance, other than the complementary structure and the favorable binding energy. Moreover, the results indicate that the method for preparing the target-specific non-antibody protein by virtual screening and bio-panning of the present invention can be used for the preparation of binder proteins optimized to have a strong binding ability and specificity to a predetermined target site.

EFFECT OF THE INVENTION

The method for preparing a target-specific non-antibody protein of the present invention can be used to provide a platform technology for the development of new bio-drugs applicable to various targets that have not been approached by the existing antibody drugs, proteins drugs, aptamers or the like. Therefore, the method of the present invention can be used for the development of progressive patient-tailored and targeted therapies, and its social and economic impacts are expected to be enormous. In addition, the target-specific protein inhibiting the EGFR domain 2 of the present invention specifically inhibits the activity of EGFR as a target of cancer therapy so as to selectively attack cancer cells other than normal cells, and thus it provides efficient therapeutic effects on cancer.

What is claimed is:

1. A method for preparing an EGFR (Epidermal Growth Factor Receptor) domain 2 specific modified non-antibody protein comprising the steps of:
   - (a) selecting non-antibody proteins having a structural complementarity with the target site of EGFR domain 2 in a non-antibody protein library;
   - (b) calculating a binding energy of the selected non-antibody protein and EGFR domain 2;
   - (c) selecting a non-antibody protein having a favorable binding energy among the selected non-antibody proteins;
   - (d) selecting amino acid residue having high binding energy among the interfacial amino acid residues of the selected non-antibody protein and EGFR domain 2, wherein the selected amino acid residue having high binding energy is selected from 44Lys, 107Glu, 110Glu, 114Asn, and 118Asp; and
   - (e) substituting the amino acid residue selected in step (d) with the amino acid residue having low binding energy, wherein step (e) is performed by phage display and bio-panning.

2. The method according to claim 1, wherein step (a) and step (b) are performed sequentially or at the same time.

3. The method according to claim 1, wherein the non-antibody protein library of step (a) includes non-antibody proteins having a molecular weight of 10 to 40 kDa, selected from human proteins, and capable of forming any one or more of monomers, homodimers, and homotrimers.

4. The method according to claim 1, wherein the library of step (a) is constructed by a method comprising the steps of:
   - (i) selecting proteins having a molecular weight of 10 to 40 kDa from the human proteins;
   - (ii) excluding membrane proteins and antibody proteins from the selected proteins in step (i);
   - (iii) selecting proteins having 10 or fewer known interactions from the rest of the proteins in step (ii); and
   - (iv) selecting proteins capable of forming any one or more of monomers, homodimers, and homotrimers from the selected proteins in step (iii).

5. The method according to claim 1, wherein the selection in step (a) is performed by docking simulation.

6. The method according to claim 5, wherein the docking simulation of step (a) is a step of selecting non-antibody proteins that bind with a predetermined number or more of target amino acid residues of EGFR domain 2.

7. The method according to claim 1, wherein in step (a), the number of the target residues is 28, and the predetermined number is 10.

* * * * *

```
                              SEQUENCE LISTING

<160> NUMBER OF SEQ ID NOS: 9

<210> SEQ ID NO 1
<211> LENGTH: 420
<212> TYPE: PRT
<213> ORGANISM: Homo sapiens
<220> FEATURE:
<221> NAME/KEY: DOMAIN
<222> LOCATION: (166)..(309)
<223> OTHER INFORMATION: Domain 2 of EGFR

<400> SEQUENCE: 1

Met Glu Glu Lys Lys Val Cys Gln Gly Thr Ser Asn Lys Leu Thr Gln
  1               5                  10                  15

Leu Gly Thr Phe Glu Asp His Phe Leu Ser Leu Gln Arg Met Phe Asn
             20                  25                  30

Asn Cys Glu Val Val Leu Gly Asn Leu Glu Ile Thr Tyr Val Gln Arg
         35                  40                  45

Asn Tyr Asp Leu Ser Phe Leu Lys Thr Ile Gln Glu Val Ala Gly Tyr
     50                  55                  60

Val Leu Ile Ala Leu Asn Thr Val Glu Arg Ile Pro Leu Glu Asn Leu
 65                  70                  75                  80

Gln Ile Ile Arg Gly Asn Met Tyr Tyr Glu Asn Ser Tyr Ala Leu Ala
                 85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
```

```
                    305                 310                 315                 320

Phe Lys Asp Ser Leu Ser Ile Asn Ala Thr Asn Ile Lys His Phe Lys
                        325                 330                 335

Asn Cys Thr Ser Ile Ser Gly Asp Leu His Ile Leu Pro Val Ala Phe
                        340                 345                 350

Arg Gly Asp Ser Phe Thr His Thr Pro Pro Leu Asp Pro Gln Glu Leu
                        355                 360                 365

Asp Ile Leu Lys Thr Val Lys Glu Ile Thr Gly Phe Leu Leu Ile Gln
                370                 375                 380

Ala Trp Pro Glu Asn Arg Thr Asp Leu His Ala Phe Glu Asn Leu Glu
        385                 390                 395                 400

Ile Ile Arg Gly Arg Thr Lys Gln His Gly Gln Phe Ser Leu Ala Val
                        405                 410                 415

Val Ser Leu Asn
                420

<210> SEQ ID NO 2
<211> LENGTH: 144
<212> TYPE: PRT
<213> ORGANISM: Homo sapiens

<400> SEQUENCE: 2

Met Ser Ser Ile Leu Pro Phe Thr Pro Pro Ile Val Lys Arg Leu Leu
        1               5                   10                  15

Gly Trp Lys Lys Gly Glu Gln Asn Gly Gln Glu Lys Trp Cys Glu
                        20                  25                  30

Lys Ala Val Lys Ser Leu Val Lys Lys Leu Lys Lys Thr Gly Gln Leu
                        35                  40                  45

Asp Glu Leu Glu Lys Ala Ile Thr Thr Gln Asn Val Asn Thr Lys Cys
                50                  55                  60

Ile Thr Ile Pro Arg Ser Leu Asp Gly Arg Leu Gln Val Ser His Arg
        65                  70                  75                  80

Lys Gly Leu Pro His Val Ile Tyr Cys Arg Leu Trp Arg Trp Pro Asp
                        85                  90                  95

Leu His Ser His His Glu Leu Arg Ala Met Glu Leu Cys Glu Phe Ala
                        100                 105                 110

Phe Asn Met Lys Lys Asp Glu Val Cys Val Asn Pro Tyr His Tyr Gln
                        115                 120                 125

Arg Val Glu Thr Pro Val Leu Pro Pro Val Leu Val Pro Arg His Thr
                130                 135                 140

<210> SEQ ID NO 3
<211> LENGTH: 144
<212> TYPE: PRT
<213> ORGANISM: Artificial Sequence
<220> FEATURE:
<223> OTHER INFORMATION: Clone 6 of 1OZJ

<400> SEQUENCE: 3

Met Ser Ser Ile Leu Pro Phe Thr Pro Pro Ile Val Lys Arg Leu Leu
        1               5                   10                  15

Gly Trp Lys Lys Gly Glu Gln Asn Gly Gln Glu Lys Trp Cys Glu
                        20                  25                  30

Lys Ala Val Lys Ser Leu Val Lys Lys Leu Lys Ser Thr Gly Gln Leu
                        35                  40                  45

Asp Glu Leu Glu Lys Ala Ile Thr Thr Gln Asn Val Asn Thr Lys Cys
                50                  55                  60
```

```
Ile Thr Ile Pro Arg Ser Leu Asp Gly Arg Leu Gln Val Ser His Arg
 65                  70                  75                  80

Lys Gly Leu Pro His Val Ile Tyr Cys Arg Leu Trp Arg Trp Pro Asp
                 85                  90                  95

Leu His Ser His His Glu Leu Arg Ala Met Gly Leu Cys Ser Phe Ala
            100                 105                 110

Phe Asn Met Lys Lys Leu Glu Val Cys Val Asn Pro Tyr His Tyr Gln
        115                 120                 125

Arg Val Glu Thr Pro Val Leu Pro Pro Val Leu Pro Arg His Thr
    130                 135                 140

<210> SEQ ID NO 4
<211> LENGTH: 144
<212> TYPE: PRT
<213> ORGANISM: Artificial Sequence
<220> FEATURE:
<223> OTHER INFORMATION: Clone 7 of 1OZJ

<400> SEQUENCE: 4

Met Ser Ser Ile Leu Pro Phe Thr Pro Pro Ile Val Lys Arg Leu Leu
  1               5                  10                  15

Gly Trp Lys Lys Gly Glu Gln Asn Gly Gln Glu Lys Trp Cys Glu
                 20                  25                  30

Lys Ala Val Lys Ser Leu Val Lys Lys Leu Lys Leu Thr Gly Gln Leu
             35                  40                  45

Asp Glu Leu Glu Lys Ala Ile Thr Thr Gln Asn Val Asn Thr Lys Cys
         50                  55                  60

Ile Thr Ile Pro Arg Ser Leu Asp Gly Arg Leu Gln Val Ser His Arg
 65                  70                  75                  80

Lys Gly Leu Pro His Val Ile Tyr Cys Arg Leu Trp Arg Trp Pro Asp
                 85                  90                  95

Leu His Ser His His Glu Leu Arg Ala Met Ala Leu Cys Ala Phe Ala
            100                 105                 110

Phe Met Met Lys Lys Cys Glu Val Cys Val Asn Pro Tyr His Tyr Gln
        115                 120                 125

Arg Val Glu Thr Pro Val Leu Pro Pro Val Leu Pro Arg His Thr
    130                 135                 140

<210> SEQ ID NO 5
<211> LENGTH: 144
<212> TYPE: PRT
<213> ORGANISM: Artificial Sequence
<220> FEATURE:
<223> OTHER INFORMATION: Clone 9 of 1OZJ

<400> SEQUENCE: 5

Met Ser Ser Ile Leu Pro Phe Thr Pro Pro Ile Val Lys Arg Leu Leu
  1               5                  10                  15

Gly Trp Lys Lys Gly Glu Gln Asn Gly Gln Glu Lys Trp Cys Glu
                 20                  25                  30

Lys Ala Val Lys Ser Leu Val Lys Lys Leu Lys Ala Thr Gly Gln Leu
             35                  40                  45

Asp Glu Leu Glu Lys Ala Ile Thr Thr Gln Asn Val Asn Thr Lys Cys
         50                  55                  60

Ile Thr Ile Pro Arg Ser Leu Asp Gly Arg Leu Gln Val Ser His Arg
 65                  70                  75                  80

Lys Gly Leu Pro His Val Ile Tyr Cys Arg Leu Trp Arg Trp Pro Asp
```

85                  90                  95
Leu His Ser His His Glu Leu Arg Ala Met Gln Leu Cys Ile Phe Ala
                100                 105                 110

Phe Leu Met Lys Lys Pro Glu Val Cys Val Asn Pro Tyr His Tyr Gln
            115                 120                 125

Arg Val Glu Thr Pro Val Leu Pro Pro Val Leu Val Pro Arg His Thr
        130                 135                 140

<210> SEQ ID NO 6
<211> LENGTH: 432
<212> TYPE: DNA
<213> ORGANISM: Homo sapiens

<400> SEQUENCE: 6
atgtcgtcca tcctgccttt cactcccccg atcgtgaagc gcctgctggg ctggaagaag      60
ggcgagcaga acgggcagga ggagaaatgg tgcgagaagg cggtcaagag cctggtcaag     120
aaactcaaga agacggggca gctggacgag ctggagaagg ccatcaccac gcagaacgtc     180
aacaccaagt gcatcaccat ccccaggtcc ctggatggcc ggttgcaggt gtcccatcgg     240
aaggggctcc ctcatgtcat ctactgccgc tgtggcgat ggccagacct gcacagccac      300
cacgagctac gggccatgga gctgtgtgag ttcgccttca atatgaagaa ggacgaggtc     360
tgcgtgaatc cctaccacta ccagagagta gagacaccag ttctacctcc tgtgttggtg     420
ccacgccaca ca                                                         432

<210> SEQ ID NO 7
<211> LENGTH: 432
<212> TYPE: DNA
<213> ORGANISM: Artificial Sequence
<220> FEATURE:
<223> OTHER INFORMATION: Clone 6 of 1OZJ

<400> SEQUENCE: 7
atgtcgtcca tcctgccttt cactcccccg atcgtgaagc gcctgctggg ctggaagaag      60
ggcgagcaga acgggcagga ggagaaatgg tgcgagaagg cggtcaagag cctggtcaag     120
aaactcaaga gcacggggca gctggacgag ctggagaagg ccatcaccac gcagaacgtc     180
aacaccaagt gcatcaccat ccccaggtcc ctggatggcc ggttgcaggt gtcccatcgg     240
aaggggctcc ctcatgtcat ctactgccgc tgtggcgat ggccagacct gcacagccac      300
cacgagctac gggccatggg tctgtgttcc ttcgccttca atatgaagaa gttggaggtc     360
tgcgtgaatc cctaccacta ccagagagta gagacaccag ttctacctcc tgtgttggtg     420
ccacgccaca ca                                                         432

<210> SEQ ID NO 8
<211> LENGTH: 432
<212> TYPE: DNA
<213> ORGANISM: Artificial Sequence
<220> FEATURE:
<223> OTHER INFORMATION: Clone 7 of 1OZJ

<400> SEQUENCE: 8
atgtcgtcca tcctgccttt cactcccccg atcgtgaagc gcctgctggg ctggaagaag      60
ggcgagcaga acgggcagga ggagaaatgg tgcgagaagg cggtcaagag cctggtcaag     120
aaactcaagc ttacggggca gctggacgag ctggagaagg ccatcaccac gcagaacgtc     180
aacaccaagt gcatcaccat ccccaggtcc ctggatggcc ggttgcaggt gtcccatcgg     240

-continued

```
aaggggctcc ctcatgtcat ctactgccgc ctgtggcgat ggccagacct gcacagccac    300
cacgagctac gggccatggg tctgtgtgcg ttcgccttca tgatgaagaa gtgtgaggtc    360
tgcgtgaatc cctaccacta ccagagagta gagacaccag ttctacctcc tgtgttggtg    420
ccacgccaca ca                                                         432

<210> SEQ ID NO 9
<211> LENGTH: 432
<212> TYPE: DNA
<213> ORGANISM: Artificial Sequence
<220> FEATURE:
<223> OTHER INFORMATION: Clone 9 of 1OZJ

<400> SEQUENCE: 9
atgtcgtcca tcctgccttt cactcccccg atcgtgaagc gcctgctggg ctggaagaag     60
ggcgagcaga acgggcagga ggagaaatgg tgcgagaagg cggtcaagag cctggtcaag    120
aaactcaagg cgacggggca gctggacgag ctggagaagg ccatcaccac gcagaacgtc    180
aacaccaagt gcatcaccat ccccaggtcc ctggatggcc ggttgcaggt gtcccatcgg    240
aaggggctcc ctcatgtcat ctactgccgc ctgtggcgat ggccagacct gcacagccac    300
cacgagctac gggccatgca gctgtgtatt ttcgccttcc tgatgaagaa gccggaggtc    360
tgcgtgaatc cctaccacta ccagagagta gagacaccag ttctacctcc tgtgttggtg    420
ccacgccaca ca                                                         432
```